United States Patent [19]
Wampler et al.

[11] Patent Number: 6,139,489
[45] Date of Patent: Oct. 31, 2000

[54] SURGICAL DEVICE WITH INTEGRALLY MOUNTED IMAGE SENSOR

[75] Inventors: Scott D. Wampler, Westchester, Ohio; Leo J. Nolan, Las Vegas, Nev.; John P. Verschoor; John V. Hunt, both of Cincinnati, Ohio; Hal H. Katz, Westchester, Ohio

[73] Assignee: Ethicon Endo-Surgery, Inc., Cincinnati, Ohio

[21] Appl. No.: 09/412,479

[22] Filed: Oct. 5, 1999

[51] Int. Cl.[7] ..................................................... A61B 1/05
[52] U.S. Cl. ........................................... 600/109; 600/129
[58] Field of Search ................................... 600/129, 210, 600/109

[56] References Cited

U.S. PATENT DOCUMENTS

| | | | |
|---|---|---|---|
| 2,055,188 | 9/1936 | Wappler et al. | 600/129 |
| 3,799,150 | 3/1974 | Bonnet | 600/129 |
| 4,391,282 | 7/1983 | Ando et al. | 600/109 |
| 4,605,009 | 8/1986 | Pourcelot et al. | 600/109 |
| 5,536,234 | 7/1996 | Niewman | 600/129 |
| 5,667,480 | 9/1997 | Knight et al. | 600/212 |
| 5,685,824 | 11/1997 | Takei | 600/129 |
| 5,722,934 | 3/1998 | Knight et al. | 600/210 |
| 5,725,479 | 3/1998 | Knight et al. | 600/210 |
| 5,827,176 | 10/1998 | Tanaka et al. | 600/129 |
| 5,865,726 | 2/1999 | Katsurada et al. | 600/129 |
| 5,902,315 | 5/1999 | DuBois | 600/210 |
| 5,921,916 | 7/1999 | Aeikens et al. | 600/129 |

*Primary Examiner*—Paul J. Hirsch
*Attorney, Agent, or Firm*—Dean Garner

[57] ABSTRACT

A surgical device for use with a video display and for retracting, viewing, and accessing tissue is described. The surgical device comprises an elongated platform and a concave head connected to a distal end of the platform. The concave head defines a cavity that provides a working space for an end-effector of an instrument. The surgical device further comprises an image sensor attached to the inside of the concave head so that tissue within the working space may be imaged by the image sensor to provide an electrical signal for a video display. The surgical device further comprises an illumination means for illuminating tissue within and adjacent to the cavity of the concave head. A power source is provided for powering the image sensor and the illumination means. A handle is attached to the proximal end of the platform.

22 Claims, 6 Drawing Sheets

SURGICAL DEVICE WITH INTEGRALLY MOUNTED IMAGE SENSOR

FIELD OF THE INVENTION

The present invention relates generally to surgical instruments and video endoscopy. In particular, the present invention relates to an endoscopic instrument for harvesting a section of a blood vessel from a surgical patient.

BACKGROUND OF THE INVENTION

The advantages of using endoscopic visualization during surgical procedures on patients are well known. Such procedures are minimally invasive, result in shortened hospital stays, more rapid recovery, less cosmetic damage, and lower overall costs compared to conventional "open" procedures.

Surgical endoscopic instruments and procedures are also well known for removing a section of a blood vessel from a surgical patient for use in another part of the patient's body or for transplanting into a second patient's body. An endoscope and method for vein removal is described in U.S. Pat. No. Re. 36,043 issued to Knighton. The endoscope has a lumen extending longitudinally for receiving at least one instrument and includes means for viewing an area adjacent the distal end of the lumen. In Knighton ('043), an image of the tissue is transmitted optically through a transmission conduit from the distal end of the device to the proximal end. The image is converted to an electrical signal by an external sensor for transmission to an external monitor. The illumination source is also external and operatively connected to the transmission conduit. The fiber optic viewing and illumination portions of the endoscope are separable from the device for cleaning and reuse. The device used for the method described in Knighton ('043), however, does not include a structure on its distal end for creating an unobstructed working space near the surgical site for dissection of the vessel. The device described also must be used with a separate light source, camera, camera controller, and video monitor. This equipment costs several thousand dollars and requires cleaning and maintenance prior to each use. The portions of the visualization system within the surgical sterile field must also be sterilized or replaced prior to use on each patient, adding to the cost of the surgical procedure.

Another example of such a device is disclosed in U.S. Pat. Nos. 5,722,934 and 5,667,480, issued to Knight, et al, which are hereby incorporated herein by reference. Knight describes in '934 and '480 a method and devices, respectively, for endoscopically removing a vessel from a patient's body. A longitudinal lumen is provided in the devices so that they may be used in combination with conventional, reusable endoscopes. An incision is first made in the patient's body near the identified vessel. An optical dissector is inserted through the incision and the endoscope is then inserted into a channel running longitudinally through the optical dissector. The tissue is optically dissected away from the surface of the vessel with the optical dissector. The optical dissector has a concave head mounted on the distal end to separate tissue from the distal end of the endoscope and to create an initial space around the vessel to be harvested. The optical dissector and endoscope are then withdrawn from the body and an optical retractor is inserted into the body through the incision. The endoscope is inserted into a channel running longitudinally through the optical retractor, which is then used to retract the dissected tissue away from the surface of the vessel. A concave head attached to the distal end of the optical retractor is provided to facilitate the retraction of tissue away from the vessel. The concave head for the optical retractor is larger than the concave head for the optical dissector, and thus provides a working space around the vessel to be harvested. The vessel and its side branches are then dissected, ligated, and transected. The vessel is then removed from the body through the incision. This surgical method is especially suited for removal of the saphenous vein of the leg, to be used as a graft in a coronary artery bypass graft (CABG) procedure for the same patient. Patients who have undergone this endoscopic surgical procedure for removal of the saphenous vein in the leg have experienced significantly less pain during recovery than patients who have undergone the more traditional open surgical procedure in which an incision is made for almost the entire length of the patient's leg. Using the endoscopic procedure as compared to using the open procedure also diminishes recovery time and associated complications.

Despite the advances in the surgical art provided by the method and devices described by Knight, needing to use the devices with a separate, conventional endoscopic visualization system also presents some of the same disadvantages as noted for the instruments used in the method disclosed by Knighton. The initial costs of the capital equipment, providing space in the operating room for the equipment, maintenance, cleaning, and sterilization, all contribute to the costs for the surgical procedure. In addition, performing the endoscopic vessel harvesting procedure has an associated learning curve. Managing the conventional endoscopic imaging equipment and cables while mastering the surgical technique is an additional burden on the surgeon. Another limitation of the instruments in the prior art is access. The length of the optical retractor cannot be longer than the length of the endoscope that is inserted into the longitudinal lumen of the optical retractor. This is because the endoscope must extend to the distal end of the optical retractor to view the tissue being dissected. This length limitation may adversely affect the access of the optical retractor to the desired surgical site for some procedures.

The vessel harvesting instruments described thus far employ conventional, endoscopic imaging techniques. Conventional endoscopes are constructed such that an objective lens and an eyepiece are disposed at opposite end portions of optical fibers for transmitting an image. The image of an article to be observed is made to focus at one end face of the optical fibers and a transmitted image being transmitted through the optical fibers and appearing on the other end face is observed through the eyepiece. More recently, endoscopes have been constructed in which an image sensor is used to replace the eyepiece and convert an optical image focused on the sensor into electrical signals. The image sensor typically includes an array of light detecting elements, where each element produces a signal corresponding to the intensity of light impinging on that element when an image is focused on the array. These signals may then be used, for example, to display a corresponding image on a monitor or otherwise used to provide information about the optical image.

One very common type of image sensor is a CCD (Charged Coupled Device). CCDs have been improved greatly during the last several years, and now provide images with very good resolution. Integrated circuit chips containing a CCD image sensor, however, have a relatively low yield during manufacture and are expensive due to the specialized processing involved. The CCDs also are highly complex and consume a relatively large amount of power. A CCD also requires an array of different voltages supplied to different parts of the chip with multiple electrical power lines. Because of their size, CCDs are typically mounted on the proximal portion of endoscopic medical instruments where minimal size is less important then on the distal end of the instruments. The CCD must be used in combination with a video-processing device in order to convert the image into an electrical format that can be used by a video display. The video processing device may be constructed on a relatively small chip and mounted in the medical instrument, but the device is typically mounted inside a separate tower unit along with a power source, light source, video display, and other required components.

CCDs have low sensitivity to light and therefore require a very intense light source. Commercially available, CCD base imaging systems contain a high intensity, xenon light source in the tower unit. The light is transmitted through an optical fiber to the distal end of the instrument in order to illuminate the image. The intensity of the light transmitted is a function of the length and orientation of the optical fibers. Energy losses are very significant for optical fibers which are several feet long (in order to reach from the handheld instrument to the tower unit) and have numerous bends, such as in a flexible optical transmission cable.

A much less expensive type of image sensor is formed as an integrated circuit using a CMOS (Complementary Metal Oxide Semiconductor) process. In such a CMOS type image sensor, a photodiode or phototransistor (or other suitable device) is used as the light-detecting element, where the conductivity of the element corresponds to the intensity of light impinging on the element. The variable signal thus generated by the light-detecting element is an analog signal whose magnitude is approximately proportional (within a certain range) to the amount of light impinging on the element. An example of a medical device using a CMOS chip is given in U.S. Pat. No. 5,817,015 issued to Adair on Oct. 6, 1998, and is hereby incorporated herein by reference.

It is known to form these light-detecting elements in a two-dimensional core array that is addressable by row and column. Once a row of elements has been addressed, the analog signals from each of the light detecting elements in the row are coupled to the respective columns in the array. In some CMOS based systems, an A/D (Analog-to-Digital) converter may then be used to convert the analog signals on the columns to digital signals so as to provide only digital signals at the output of the image sensor chip. These signals may then be transmitted to a video display for viewing of the image. Examples of this type of video format include the PAL format commonly used for European televisions, and the high resolution, S video format, used, for example, in surgical operating rooms. (Most CCD based endoscopic systems also use the S video format.) Other CMOS based systems send an analog signal to the video display. An example of this type of format is the NTSC format such as used for the standard television in the United States. The latter is a very popular format, therefore, for CMOS based systems, due to the huge number of NTSC formatted televisions available.

CMOS image sensors are generally several times more sensitive to light than CCD image sensors. As a result, the light intensity required to illuminate the image when using a CMOS system (typically less than or equal to one lux) is much less than what must be provided by the light source for a CCD system. In fact, a very low power light source, such as a tungsten filament, incandescent, penlight bulb, placed near the area being imaged, or used with a short length of a light transmitting element such as an acrylic rod, is sufficient for the CMOS system to obtain a good image. The low power light source and transmitting element are small enough to place inside of a handheld, endoscopic medical instrument. The xenon light source for the CCD system, however, is necessarily larger than could be placed into an endoscopic medical instrument, and therefore is mounted into the tower unit and used with a long optical fiber transmission element having the inherent losses already described.

CMOS image sensors require very little electrical power and it is practical to use small (in the range of 6–9 VDC) batteries to operate them, although a CMOS image sensor can also be used with a conventional DC power supply connected to a wall outlet. CCD image sensors, however, require much more power to operate (typically about 60 volt-amps) transmitted through multiple power lines and it is not practical to operate them for prolonged periods of time with batteries.

From the foregoing discussion, it is evident that it would be practical and advantageous to eliminate the tower unit of a CCD based endoscopic visualization system by using instead a CMOS based visualization system. One of or both the light source and the power source can be integrated into a handheld instrument to operate the CMOS image sensor constructed into the viewing end of the instrument. The output signal of the CMOS image sensor could then be connected to any one of a number of video displays, including conventional televisions, depending on the video format chosen. By eliminating the tower unit, the capital equipment cost to the hospital of performing a surgical procedure such as saphenous vein harvesting could be greatly diminished. This would make such surgical procedures much more economically feasible in hospitals not already having the required number of expensive, endoscopic visualization systems. In addition, the space available in the typically crowded operating room could be increased. And because of the relatively low cost of CMOS based imaging devices, it would be practical to construct endoscopic surgical instruments which are single patient use disposable so that cleaning and resterilization of the instrument would not be necessary.

A surgical device is needed, therefore, for retracting, viewing, and accessing tissue, having the features and advantages of the optical retractor described in Knight ('480) and constructed integrally with a low cost, imaging sensor. Particularly, what is needed is an inexpensive, imaging retractor that incorporates a CMOS chip imaging sensor and an illumination means for viewing the tissue being operated on, thereby diminishing the need for a separate tower unit as is used with convention CCD based imaging systems.

SUMMARY OF THE INVENTION

A surgical device is provided for retracting, viewing, and accessing tissue, particularly for harvesting a blood vessel from a surgical patient. The surgical device comprises an elongated platform and a concave head connected to a distal end of the platform. The concave head defines a cavity therein and provides a working space for an end-effector of an instrument. An image sensor is attached to the inside of the concave head of the surgical device, whereby tissue within the working space may be imaged by the image sensor, and whereby the image sensor provides an electrical signal for a video display. An illumination means is provided for illuminating tissue within and adjacent to the cavity of the concave head. The surgical device further comprises a handle connected to the proximal end of the platform. In one embodiment, the illumination means for illuminating tissue comprises an electrically powered light source mounted within the proximal end of the platform and an elongated light transmission element contained within the platform. Light from the light source is transmitted from the proximal end of the light transmission element to its distal end. In a preferred embodiment, the image sensor comprises a complementary metal oxide semiconductor (CMOS) chip and an optical element (such as a lens) attached to the concave head, whereby light representing an image is transmitted through the optical element, captured by the CMOS chip, and processed by the CMOS chip into an electric signal for a video display.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
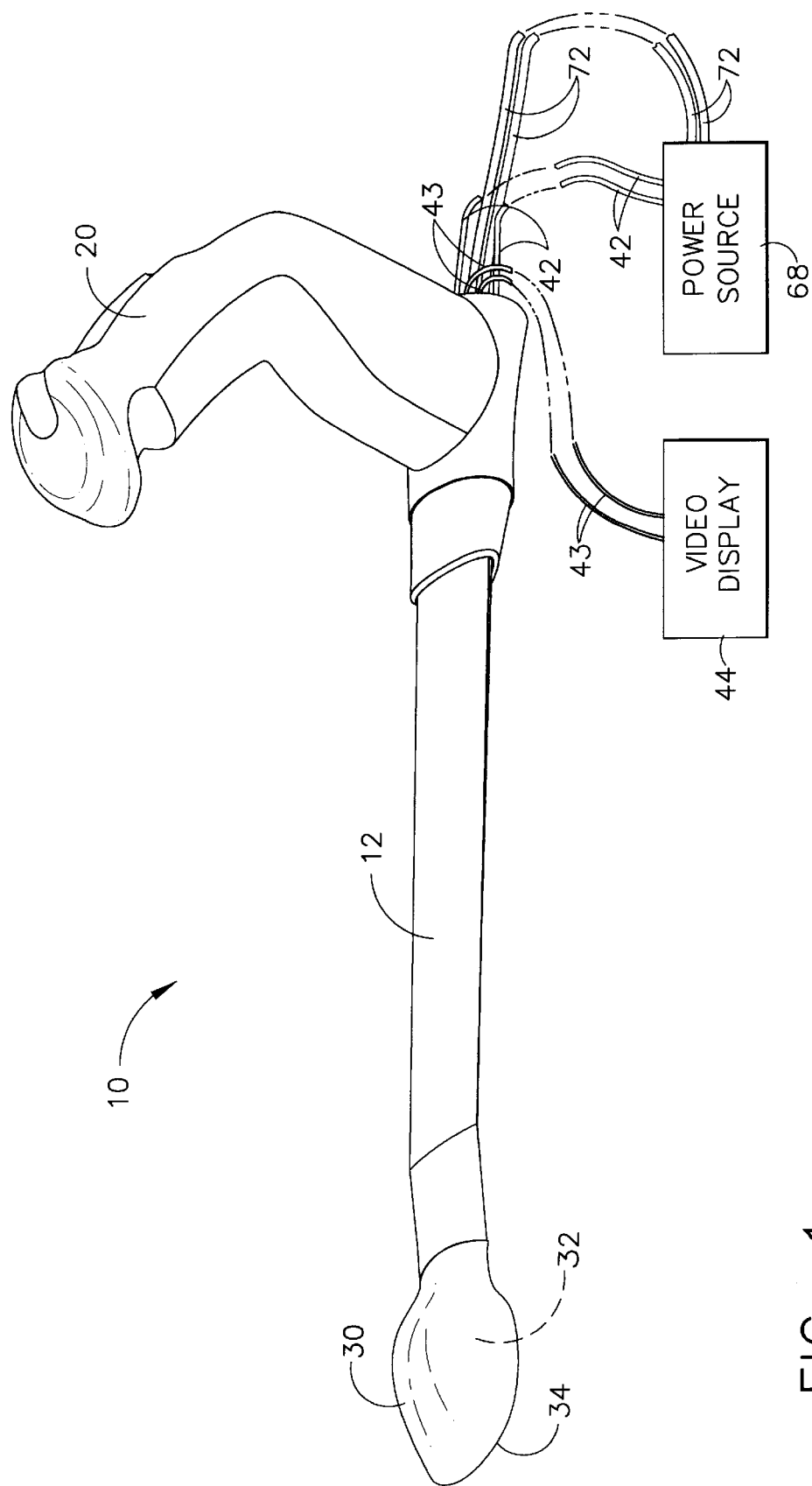
FIG. 1 illustrates the present invention, a surgical device for use with a video display (shown generically), the surgical device comprising an imaging retractor containing an image sensor and an illumination means, and a power source (shown generically).

FIG. 1 illustrates an embodiment of the present invention, an imaging retractor 10, which comprises a handle 20 connected to a concave head 30 by an elongated platform 12. Concave head 30 is spoon-shaped and has an outer peripheral edge 34 and a cavity 32 therein. Concave head 30 is preferably made of a transparent material such as polycarbonate plastic. The shape and size of the concave head 30 as shown in FIG. 1 is one example of the large variety of shapes and sizes that would could be incorporated without altering substantially the function or results obtained with the present invention.

Imaging retractor 10 further comprises a pair of signal conductors 43 (also referred to as a signal transmission means) for transmitting a digital or analog signal to a video display 44. A pair of power conductors 42 is provided for electrically attaching a power source 68 to a CMOS chip set 40 (see FIG. 2). A pair of illumination conductors 72 is provided for electrically attaching an illuminator 78 (also referred to as an illumination means 78, see FIG. 2) to power source 68. Power source 68 is adapted to provide the appropriate direct current voltages to both the CMOS chip set 40 (which may require, for example, about 6–9 VDC) and illuminator 78 (which may require, for example, about 3–6 VDC) using conventional electronic circuitry well-know to those skilled in the art. It is also possible to provide individually dedicated power sources for CMOS chip set 40 and illuminator 78. In addition, power source 68 may be physically separate from imaging retractor 10 or integrally constructed within imaging retractor 10. For example, handle 20 may contain at least one electrical battery and a simple electrical circuit for providing the required electrical power to CMOS chip set 40 and illuminator 78, as those skilled in the art will appreciate. Illumination conductors 72 and power conductors 42 may be detachably connected to either power source 68 or imaging retractor 10 by using conventional electrical connectors, thus facilitating the cleaning, sterilizing, or disposing of the imaging retractor 10.

CMOS chip set 40 contains a video-processing element and the format for the electrical signal generated may vary. Video display 44 of FIG. 1 may, for example, be a conventional, American television if CMOS chip set 40 uses the NTSC format. CMOS chip set 40 may also process an image into a PAL or S video format, and the kind of video display 44 required would therefore need to be able to receive the particular format of the signal sent by CMOS chip set 40. For the S video format, a digital monitor type of video display 44 would be required, providing very high resolution. Signal conductors 43 may be detachably connected to either video display 44 or imaging retractor 10 using conventional signal connectors (such as an RCA connector) which are well known in the art. This also facilitates the cleaning, sterilizing, or disposing of imaging retractor 10. Video display 44 may be physically separated from imaging retractor 10. Very small video displays are now commercially available so that it would also be possible to mount video display 44 onto handle 20 such as described by Green in International Publication Number WO 97/41767. For this arrangement, the video display 44 could be powered also by power source 68.

Figure 2:
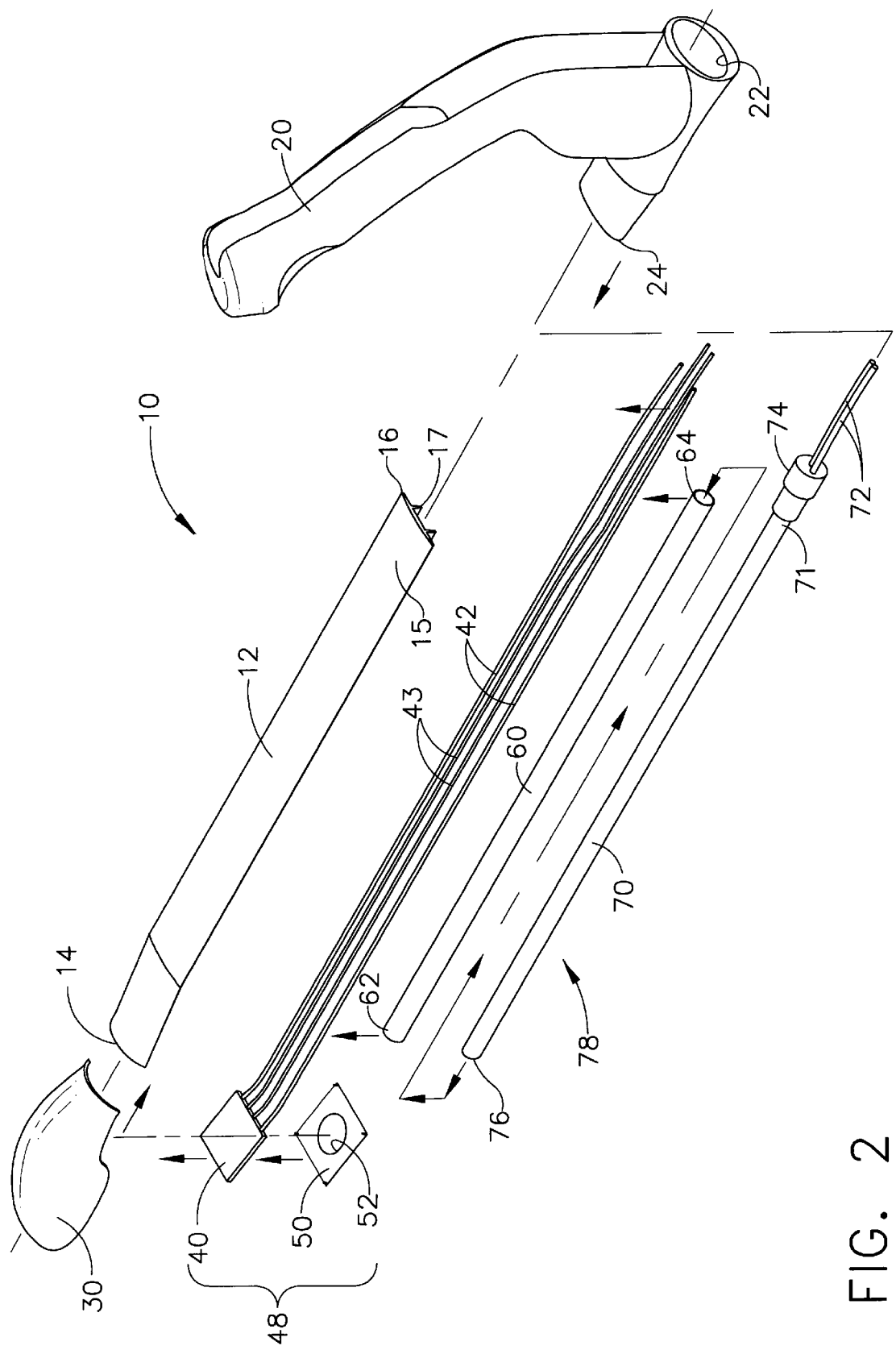
FIG. 2 is an exploded isometric view of the imaging retractor illustrated in FIG. 1.

FIG. 2 is an exploded isometric view of imaging retractor 10. Handle 20 comprises a nose 24 that attaches to a proximal end 16 of platform 12, and an opening 22. Concave head 30 similarly attaches to a distal end 14 of platform 12. Handle 20 and platform 12 are preferably made of a rigid, medical grade plastic such as polycarbonate. Platform 12 is further provided with a pair of longitudinal ribs 17 (partially visible) which are spaced apart and positioned longitudinally along an undersurface 15 of platform 12.

CMOS chip set 40 is shown in FIG. 2 relatively positioned for attachment to concave head 30, using for example a biocompatible adhesive. Signal conductors 43 and power conductors 42 are shown electrically attached to CMOS chip set 40, running longitudinally along longitudinal ribs 17 of platform 12, and inserted into nose 24 and out of opening 22 of handle 20. Signal conductors 43 and power conductors are preferably made from insulated electric wire. A suitable example of CMOS chip set 40 is commercially available as Part Number 0V7910 from Omnivision, Inc. located in Sunnyvale, Calif. This CMOS chip is a high resolution color, board-level camera featuring color NTSC or PAL, ⅓ inch CMOS Active Pixel Imager, 4.8 mm×3.6 mm image area, 2:1 scanning interlace, S-Video Y/C 75 Ohm unbalanced, S/N ratio 68 dB, sensitivity 0.2 Lux @ f1.4, operating current 6–15 volts DC, 150 mW with 75 Ohm load, and has dimensions of 14.5 mm×14.5 mm. Examples of a suitable power source 68 for the CMOS chip are a battery (possibly rechargeable), a solar panel, or a conventional AC/DC transformer.

Still referring to FIG. 2, illuminator 78 comprises a rod 70, a proximal endpiece 74, a light source 73 (see FIG. 6) inside of endpiece 74, and a hollow tube 60. Rod 70 (also referred to as a light transmission element 70) has a proximal end 71 attached to proximal endpiece 74. Illuminator conductors 72 are electrically attached to light source 73, and are preferably made from an insulated and shielded electric wire. For this embodiment, illuminator conductors 72 are electrically attached to a remotely located, direct current power source such as a battery, a solar panel, or an AC/DC transformer. Rod 70 is made from a transparent material such as clear acrylic, and is highly polished on a distal endface 76 and proximal endface 69 (see FIG. 6) on proximal end 71. Distal endface 76 and proximal endface 69 are shown in FIG. 2 to be flat surfaces, but either may also be convexedly curved to spread light or concavedly curved to focus light. Tube 60 has a proximal end 64 and a distal end 62. Tube 60 encases rod 70 for its entire length and is preferably made of a stainless steel, although other materials able to provide the necessary rigidity and prevent the escape of light transmitted from rod 70 may be used. Tube 60 is affixed with a biocompatible adhesive to platform 12 between the pair of longitudinal ribs 17 on undersurface 15. In this embodiment, tube 60, signal conductors 43, and power conductors 42 are adhered to undersurface 15 with a biocompatible adhesive. A cover 50 protects CMOS chip set 40 and holds a centrally-mounted, optical element 52 for optically improving the image onto the CMOS chip set 40. Optical element 52, for example, may be an optical lens (f1.4, for example) for focusing an image onto CMOS chip set 40. Cover 50 and optical element 52 may be molded as a single piece from an optically transparent plastic, or may be separate elements attached together. For example, optical element 52 may be made of a optical ceramic material such as glass, and bonded with a cyanoacrylate adhesive to cover 50, which is made from an injection molded, medical grade plastic. As shown in FIG. 2, CMOS chip set 40, optical element 52, and cover 50 are also referred to in combination as an image sensor 48. In another embodiment, optical element 52 may incorporate an optical filter for the selective filtering of one or more wavelengths of light. For example, optical element 52 may have an optical filter to remove the red wavelength of light.

Figure 3:
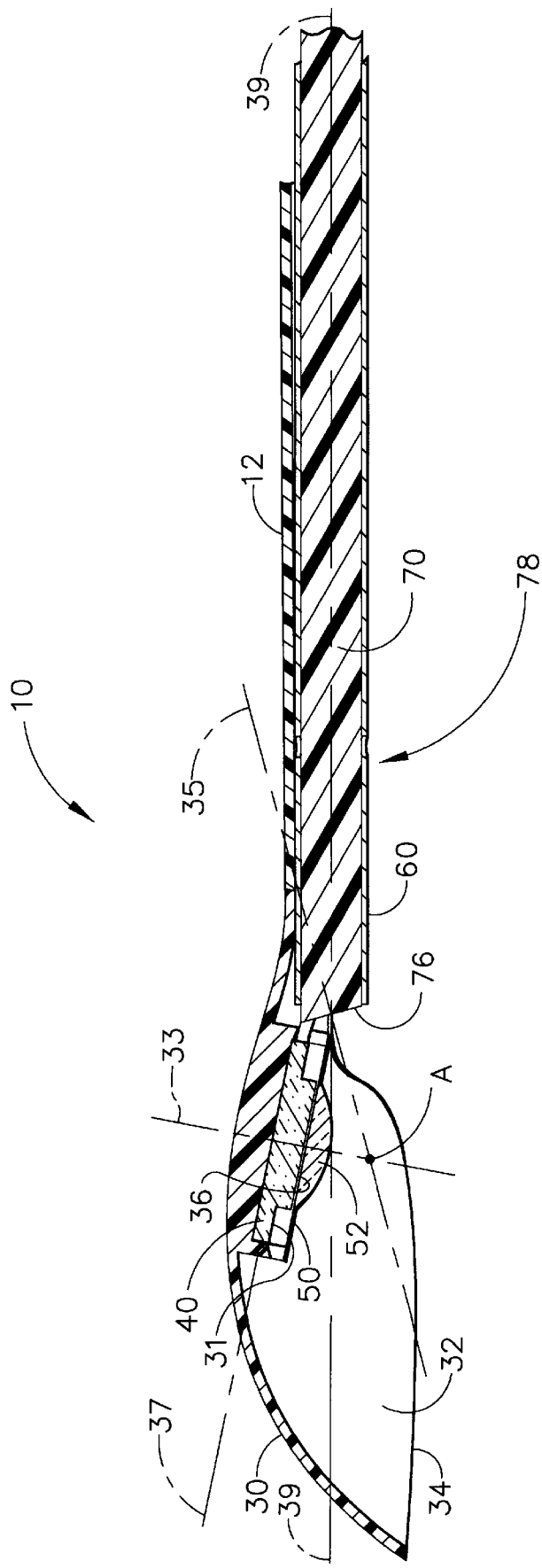
FIG. 3 is a longitudinal cross sectional view of the distal portion of the imaging retractor illustrated in FIG. 1.

FIG. 3 is a sectional view of the distal portion of imaging retractor 10. CMOS chip set 40 is held in retainer 31 inside cavity 32 of concave head 30. Retainer 31 may be molded integrally into concave head 30, or may be a separate part affixed to concave head 30 with an adhesive or other means. Optical element 52 is attached to cover 50 which is attached to retainer 31 so that optical element 52 and CMOS chip set 40 have a common viewing axis 33. A gap 36 between optical element 52 and CMOS chip set 40 may vary in width, depending on the specifications of the CMOS chip set 40 and the optical properties of the optical element 52. CMOS chip set 40, optical element 52, and illuminator 78 are assembled in an alignment that allows imaging to occur at an optimal location A. In the preferred embodiment, optimal location A is also the focal point of optical element 52 and coincides with the intersection of viewing axis 33 and a rod endface axis 35, which is perpendicular to distal endface 76 of rod 70. Optimal location A is approximately centered transversely within cavity 32. Optimal location A is where the highest intensity light from illuminator 78 impinges at the focal point of optical element 52. The optimal viewing range for imaging retractor 10, and the area where tissue dissection occurs, is in the vicinity of optimal location A. It is possible to alter the location of optimal location A by selection of the focal point of optical element 52, the orientation of optical element 52 and CMOS chip set 40, and the orientation of distal endface 76 during construction of the imaging retractor 10. Specifically, the angle formed between a retainer axis 37 and a longitudinal axis 39 may be matched with the angle formed between rod endface axis 35 and longitudinal axis 39, so that optimal location A is approximately at the focal point of the optical element 52 along viewing axis 33. For the embodiment shown in FIG. 3, the angle between retainer axis 37 and longitudinal axis 39 is approximately in the range of 10–20 degrees; and the angle between rod endface axis 35 and longitudinal axis 39 is approximately 30 degrees.

Figure 4:
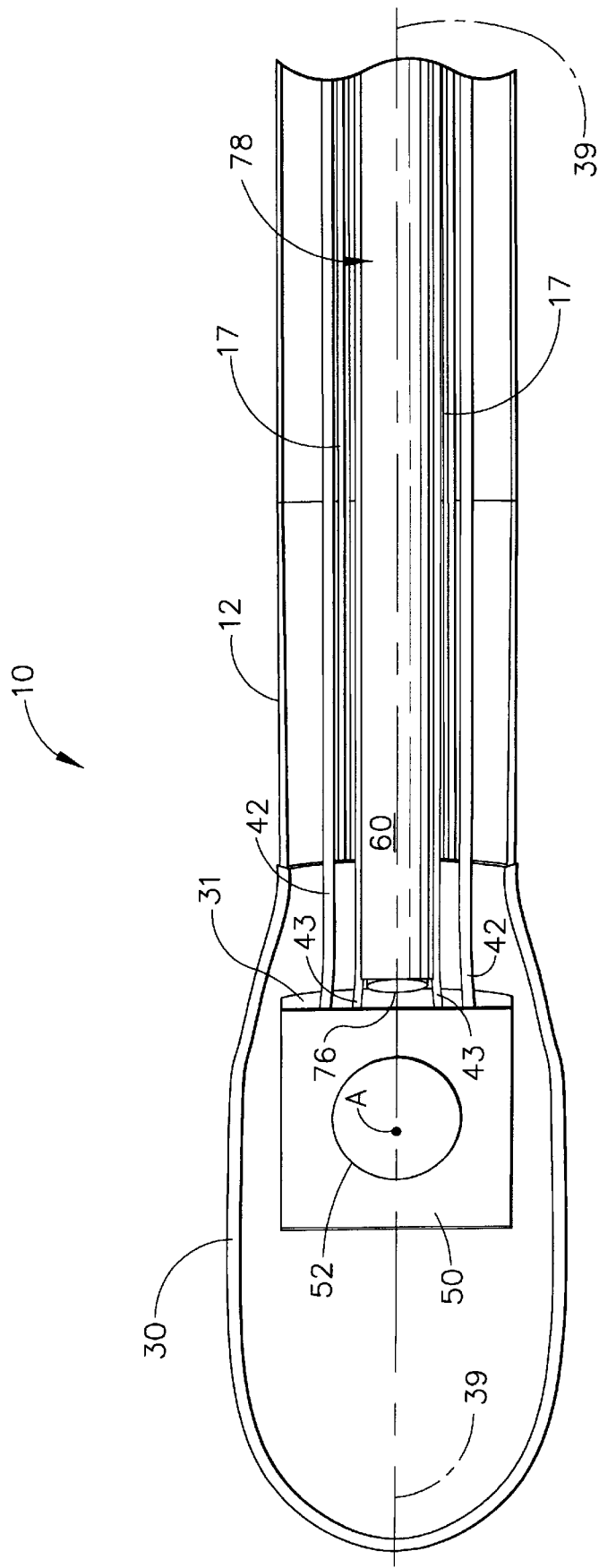
FIG. 4 is a bottom view of the distal portion of the imaging retractor illustrated in FIG. 1.

FIG. 4 is a bottom view of the distal portion of imaging retractor 10. Concave head 30 is shown on the open side. Optical element 52 and cover 50 are shown mounted inside retainer 31 so that optimal location A is centered transversely with respect to longitudinal axis 39. Rod endface 76 of illuminator 78 is also centered transversely with respect to longitudinal axis 39.

Figure 6:
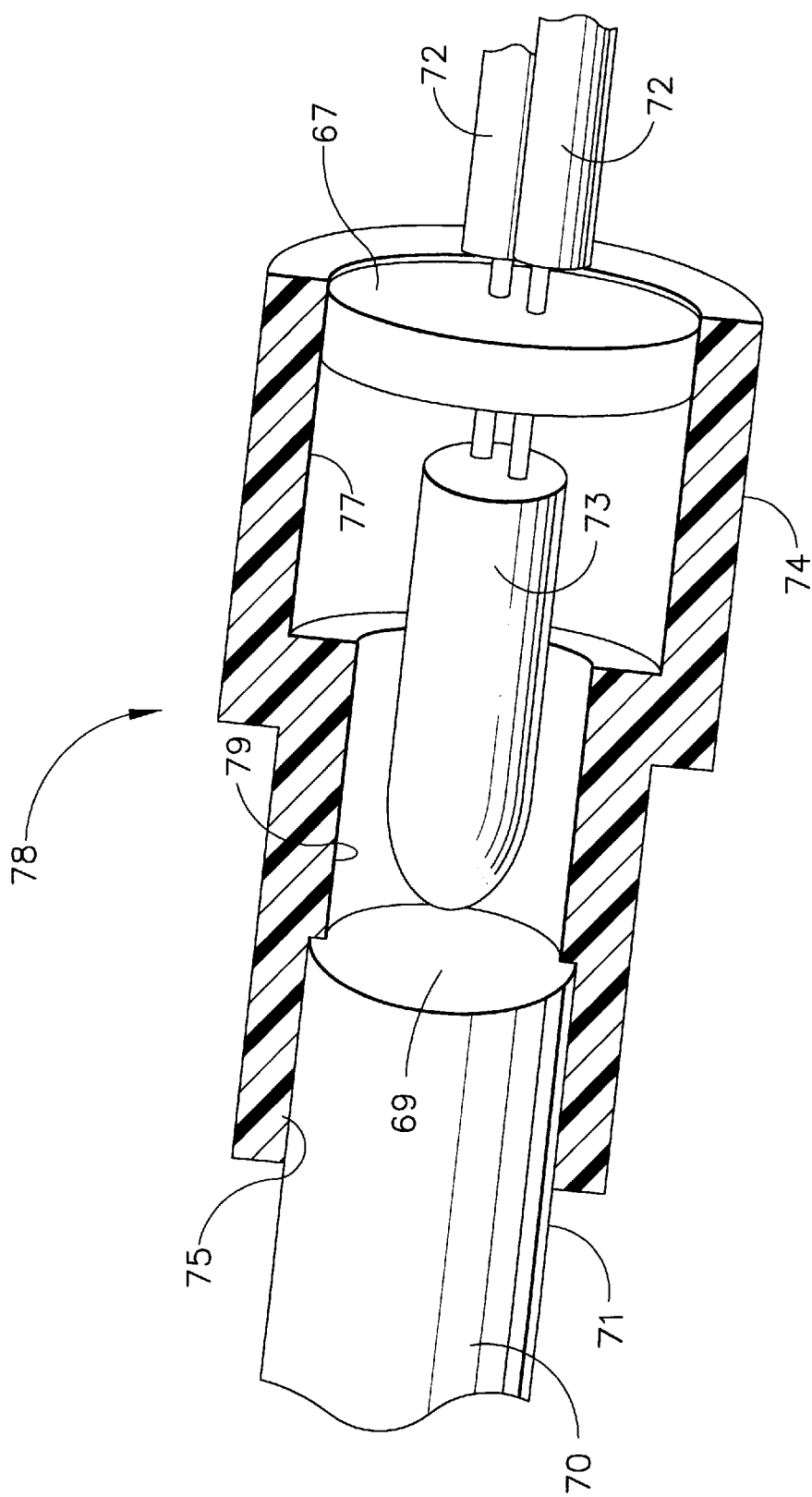
FIG. 6 is a sectional view of an electrically powered light source of an illuminator shown in FIG. 2.

FIG. 6 is an enlarged, sectional view of endpiece 74 of illuminator 78. Endpiece 74 is preferably made of a rigid, medical grade plastic. Endpiece 74 comprises a distal recess 75, an endpiece lumen 79, and a proximal recess 77, coaxially aligned with rod 70. Proximal end 71 of rod 70 is attached within distal recess 75 of proximal endpiece 74 using an adhesive or press fit. Proximal endface 69 of rod 70 is in close proximity to an electrically powered light source 73 suspended within endpiece lumen 79 by the pair of illuminator conductors 72. Illuminator conductors 42 pass through and are supported by an endcap 67 pressed or glued into a proximal recess 77 of endpiece 74. A suitable example for light source 73 is a standard, tungsten filament, flashlight bulb requiring 3.0 VDC and having a light intensity of 4000 lux @ 1.5 inches.

Figure 5:
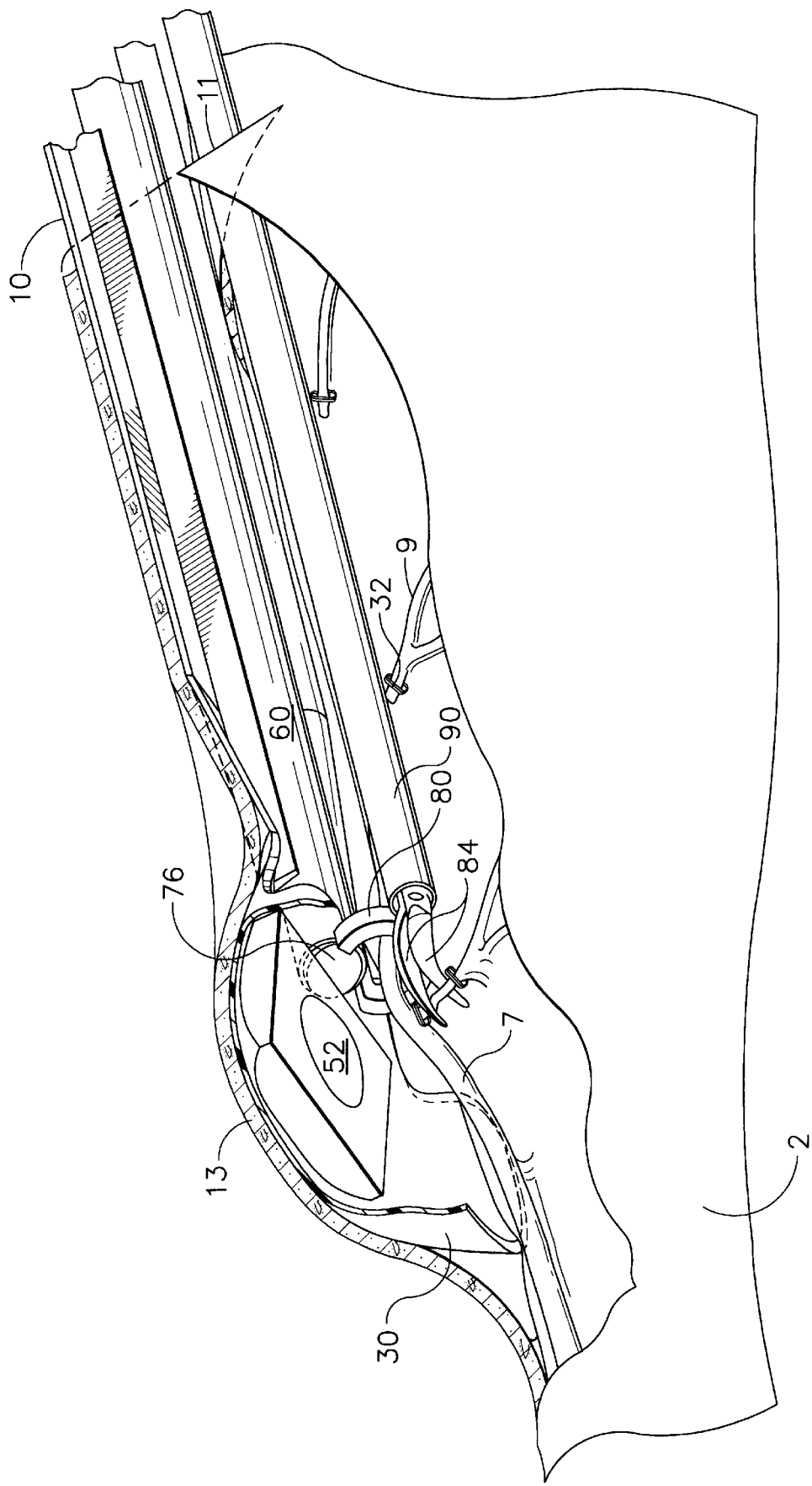
FIG. 5 illustrates the use of the imaging retractor in combination with a vessel dissector and a clip applier during a vessel harvesting surgical procedure.

FIG. 5 illustrates imaging retractor 10 being used in combination with a dissection instrument 80 and a surgical scissors 90 to remove a blood vessel 7 from a surgical patient 2. Distal endface 76 emits light from the distal end of tube 60 to illuminate the working space. Dissection instrument 80, scissors 90, and imaging retractor 10 are inserted into an incision 11 made through the skin and subcutaneous layers 13. The concave head 30 is shown lifting the skin and subcutaneous layers 13 in order to create a working space underneath concave head 30. A plurality of surgical ligation clips 92 are shown already closed onto a like plurality of side branches 9 of blood vessel 7, and the scissors 90 are shown severing the side branches 9 between the clips 92 in order to free the blood vessel 7. The portion of the blood vessel 7 being operated on, the end effectors 84 of the dissection instrument 80 and the scissors 90 are in the working space created by concave head 30 of imaging retractor 10, and in the viewing range of optical element 52. The surgeon uses the handle 20 (see FIG. 1) to advance and retract the concave head 30 axially, and to rotate the concave head 30 about longitudinal axis 39 to retract adjoining tissue from blood vessel 7. After each side branch 9 is severed, concave head 30 is advanced distally along blood vessel 7 until the next side branch 9 is within the viewing range of optical element 52. When a sufficient length of blood vessel 7 is hemostatically freed from surrounding tissue, the dissected portion of blood vessel 7 is severed with scissors 90. The instruments, 80 and 90, and imaging retractor 10, are removed from incision 11. The length of blood vessel 7 is pulled out (using a surgical grasper, for example) of the incision 11 to be used as a graft vessel elsewhere on the patient.

The surgical method described above is only one example of how the present invention may be used to retract, view, and access tissue inside a body cavity. The present invention may also be used for other surgical procedures that now will be evident to those skilled in the art.

While a preferred embodiment of the present invention has been shown and described herein, it will be obvious to those skilled in the art that such an embodiment is provided by way of example only. Numerous variations, changes, and substitutions will now occur to those skilled in the art without departing from the invention.

What is claimed is:

1. A surgical device for use with a video display, said surgical device for retracting, viewing, and accessing tissue, said surgical device comprising:
   a. an elongated platform having proximal and distal ends;
   b. a concave head connected to said distal end of said platform, said concave head defining a cavity therein, wherein said cavity provides a working space for an end effector of an instrument;
   c. an image sensor attached to the inside of said concave head, said image sensor providing an electrical signal for a video display, and a signal transmission means for transferring said electrical signal to a video display, whereby tissue within said working space may be imaged by said image sensor; and
   d. a power source for operating said image sensor.

2. The surgical device of claim 1 further comprising a handle connected to said proximal end of said platform.

3. The surgical device of claim 1 further comprising an illumination means for illuminating tissue within and adjacent to said cavity of said concave head.

4. The surgical device of claim 3 wherein said illumination means is powered by said power source.

5. The surgical device of claim 3, wherein said power source is detachably connected to said image sensor and said illumination means.

6. The surgical device of claim 3, wherein said illumination means comprises an electrically powered light source affixed within said distal end of said platform.

7. The surgical device of claim 3, wherein said illumination means comprises an electrically powered light source affixed within said proximal end of said platform, and an elongated light transmission element within said platform for transmitting light from said proximal end to said distal end of said platform.

8. The surgical device of claim 1, wherein said concave head is transparent.

9. The surgical device of claim 1, wherein said image sensor comprises an optical element and a complementary metal oxide semiconductor chip which captures light, representing an image, transmitted through said optical element and thereafter processes said image into an electrical signal for a video display.

10. The surgical device of claim 1, wherein said signal transmission means for transferring said signal to a video display comprises two electrical signal conductors detachably connected to a video display.

11. The surgical device of claim 1, wherein said platform and said handle are made of plastic.

12. A surgical device for use with a video display, said surgical device for retracting, viewing, and accessing tissue, said surgical device comprising:
   a. an elongated platform having proximal and distal ends;
   b. a concave head connected to said distal end of said platform, said concave head defining a cavity therein, wherein said cavity provides a working space for an end effector of an instrument;
   c. an image sensor attached to the inside of said concave head, said image sensor comprising a complementary metal oxide semiconductor chip which captures light, defining an image, and thereafter processes said image into an electrical signal for a video display, and a signal transmission means for transferring said signal to a video display, whereby tissue within said working space may be imaged by said image sensor; and
   d. a power source for providing electrical power to said image sensor.

13. The device of claim 12, further including a handle connected to said proximal end of said platform.

14. The device of claim 12, further including a light source attached to said proximal end of said platform and an elongated light transmission element within said platform for transmitting light from said proximal end to said distal end of said platform.

15. The surgical device of claim 12, wherein said power source is detachably connected to said image sensor and said light source.

16. The surgical device of claim 12, wherein said concave head is transparent.

17. The surgical device of claim 12, wherein said image sensor further comprises two electrical signal conductors detachably connected to a video display.

18. The surgical device of claim 12, wherein said platform and said handle are made of plastic.

19. A surgical device for use with a video display, said surgical device for retracting, viewing, and accessing tissue, said surgical device comprising:
   a. an elongated platform having proximal and distal ends, wherein said platform is made from plastic;
   b. a concave head connected to said distal end of said platform, said concave head defining a cavity therein, wherein said cavity provides a working space for an end effector of an instrument, and said concave head is made from a transparent plastic;
   c. an image sensor attached to the inside of said concave head, said image sensor comprising a complementary metal oxide semiconductor chip which captures light, defining an image, and thereafter processes said image into an electrical signal for a video display, and a signal transmission means for transferring said signal to a video display comprising two electrical signal conductors detachably connected to a video display, whereby tissue within said working space may be imaged by said image sensor; and
   d. a power source for providing electrical power to said image sensor, and said power source is detachably connected to said platform.

20. The surgical device of claim 19 further comprising a handle connected to said proximal end of said platform, wherein said handle is made from plastic.

21. The surgical device of claim 19, further comprising a light source attached to said proximal end of said platform, for illuminating tissue within and adjacent to said cavity of said concave head.

22. The surgical device of claim 19, further comprising an elongated, light transmission element having proximal and distal ends and contained in said platform, whereby light from said light source is transmitted from said proximal end to said distal end of said light transmission element.

* * * * *